(12) United States Patent
Nakashima et al.

(10) Patent No.: US 7,816,128 B2
(45) Date of Patent: Oct. 19, 2010

(54) AUTOMATIC CELL CULTIVATION APPARATUS HAVING A MULTIJOINT ROBOT

(75) Inventors: Katsumi Nakashima, Hyogo (JP); Toshihisa Doi, Hyogo (JP); Yohichi Nakamura, Hyogo (JP)

(73) Assignee: Kawasaki Jukogyo Kabushiki Kaisha, Kobe (JP)

( * ) Notice: Subject to any disclaimer, the term of this patent is extended or adjusted under 35 U.S.C. 154(b) by 1153 days.

(21) Appl. No.: 11/287,965

(22) Filed: Nov. 28, 2005

(65) Prior Publication Data

US 2006/0115889 A1 Jun. 1, 2006

(30) Foreign Application Priority Data

Nov. 29, 2004 (JP) .............................. 2004-343867

(51) Int. Cl.
*C12M 1/00* (2006.01)
*C12M 3/00* (2006.01)

(52) U.S. Cl. .................. 435/303.1; 74/490.1; 483/901; 435/286.2; 435/286.3; 435/287.3; 901/8; 901/30

(58) Field of Classification Search .............. 435/286.2, 435/286.3, 287.2, 303.1; 74/490.1; 156/345.32; 382/153; 483/901; 700/900; 901/8, 36

See application file for complete search history.

(56) References Cited

U.S. PATENT DOCUMENTS

| | | | |
|---|---|---|---|
| 3,830,701 A | 8/1974 | Stussman et al. | |
| 5,573,942 A | 11/1996 | Miyamoto | |
| 7,390,458 B2 * | 6/2008 | Burow et al. | 422/63 |
| 2001/0046689 A1 * | 11/2001 | Yahiro | 435/29 |
| 2003/0040104 A1 | 2/2003 | Barbera-Guillem | |
| 2005/0011294 A1 * | 1/2005 | Hashimoto et al. | 74/490.01 |

(Continued)

FOREIGN PATENT DOCUMENTS

EP 1270718 A1 1/2003

(Continued)

OTHER PUBLICATIONS

Fonte Loredana Di Alessio, Massimiliano Nitti, Floriana Renna, Giovanni Attolico and Archangelo Distante. "Characterizing the 3D Tracking Perfromance of an Haptic Device". Proceedings of EuroHaptics 2004, Munich Germany, Jun. 5-7, 2004.*

(Continued)

*Primary Examiner*—William H Beisner
*Assistant Examiner*—Michael Hobbs
(74) *Attorney, Agent, or Firm*—Marshall, Gerstein & Borun LLP

(57) ABSTRACT

An automatic cell cultivation apparatus is provided which is capable of conveying the culture container, exchanging the culture medium, and operating other jobs promptly by a robot. The automatic cell cultivation apparatus has a cultivation apparatus main body for cultivating cells in a culture container, and the cultivation apparatus main body is equipped with one or more incubator accommodating the culture container, a chemical suction machine for sucking chemicals in the culture container, and a multijoint robot for conveying the culture container, the multijoint robot having functions of conveying the culture container, detaching and attaching the lid of the culture container, and inclining the container when sucking chemicals in the culture container, so that cell cultivation operations can be promptly carried out by only one robot.

13 Claims, 11 Drawing Sheets

(a)

(b)

U.S. PATENT DOCUMENTS

| | | | |
|---|---|---|---|
| 2005/0084955 A1* | 4/2005 | Tamaoki et al. | 435/303.1 |
| 2005/0176138 A1* | 8/2005 | Nishimoto et al. | 435/289.1 |
| 2006/0275888 A1* | 12/2006 | Hibino et al. | 435/286.2 |

FOREIGN PATENT DOCUMENTS

| | | |
|---|---|---|
| EP | 1443103 A1 | 8/2004 |
| EP | 1548099 A1 | 6/2005 |
| EP | 1571201 A2 | 9/2005 |
| JP | 06-225753 | 8/1994 |
| JP | 2000-175678 A | 6/2000 |
| JP | 2002-262856 | 9/2002 |
| JP | 2004-089095 | 3/2004 |
| JP | 2004-267117 A | 9/2004 |
| WO | WO-2004/011593 | 2/2004 |
| WO | WO 2004/090093 * | 10/2004 |
| WO | WO-2004/090093 A1 | 10/2004 |

OTHER PUBLICATIONS

European Search Report received in EPO Application No. 05257336.7, dated Mar. 8, 2006.

Knoll et al., "Flexible Automation of Cell Culture and Tissue Engineering Tasks," American Chemical Society and American Institute of Chemical Engineering, pp. 1825-1835, 2004.

Vogt, Gerald, "Multi-axis robots bring automation to life sciences," Industrial Robot: An Industrial Journal, vol. 29, No. 1, pp. 49-52, 2002.

Nikkei Industrial News, Mar. 5, 2003, Partial translation.

"Robots bring a smooth touch to cell culture," Manufacturing Chemist, Sep. 2002, pp. 78-80.

* cited by examiner

AUTOMATIC CELL CULTIVATION APPARATUS HAVING A MULTIJOINT ROBOT

The present application claims the benefit of priority of Japanese Patent Application No. 2004-343867 filed Nov. 29, 2004. The entire text of the priority application is incorporated herein by reference in its entirety.

FIELD OF THE INVENTION

The present invention relates to an automatic cell cultivation apparatus used in regenerative medicine, research and other applications.

BACKGROUND OF THE INVENTION

Recently, so-called regenerative medicine, taking out a part of human body such as cells and tissues of skin, cartilage, bone, blood vessel, and organs, cultivating outside the body, and using in treatment of a same subject or a different patient is developed and partly put in use.

In such regenerative medicine, cells are cultivated by supplying liquid culture medium containing nutrients into culture container, seeding cells in the liquid culture medium, and cultivating in the incubator in prescribed culture conditions. At this time, culture medium exchanging operation that discharging the spent culture medium and charging fresh culture medium is carried out periodically, and subculture operation are performed. In general, such operation manually operated by workers, but this work takes much time and labor. Besides, a large cost is required for preventing from contamination by workers. Accordingly, it has been considered to develop an apparatus using robots.

As prior art of this kind, an automatic culture medium exchange apparatus is proposed (for example, see Japanese Laid-Open Patent Publication No. 2002-262856 (pages 5-7, FIGS. 1 and 2)), in which culture containers are taken out of multi-stage incubator by an orthogonal conveying robot, dismounted culture containers are conveyed to predetermined position by conveyor, the lids of culture containers are removed by an dedicated lid opening robot, containers are further conveyed to predetermined position by conveyor, and culture medium in culture containers is discharged and supplied by dedicated machine.

The patent document described above also discloses an automatic culture cell exchange method for realizing the operation of controlling robots by computer, inclining the container when exchanging the liquid culture medium, sucking the spent culture medium by pipet, and supplying a fresh culture medium, by an exclusive machine.

However, since the automatic culture medium exchange apparatus of the above patent document is of orthogonal type, a wide working space is needed when taking out culture containers from multi-stage incubator, conveying the culture containers to cultivation operation unit and removing lids, discharging and supplying culture medium, and in addition, the position or direction of gripped object cannot be changed. Moreover, because a series of operations must be done while using many robots in cooperation, complicated control is needed and much time is consumed. Using plural robots, countermeasures for prevention of contamination are also essential.

Meanwhile, in cell cultivation, cells grow by sticking to the bottom of the culture container, and no longer grow when the bottom is full. Accordingly, subculture is needed for dispensing the grown cells into plural culture containers. In this subculture, a small amount of cell exfoliation agent (for example, trypsin) is supplied (added) in the container, and cells sticking to the bottom of culture container are exfoliated. However, this cell exfoliation agent dissolves protein and is hence harmful for cells, and it is desired to use in a small amount and in a short time. For example, in manual operation for exfoliating cells by workers, using a small amount of chemical, the small amount of chemical is distributed to the whole surface by inclining the culture container two-dimensionally, and entire cells are exfoliated.

Because it is difficult for the conventional orthogonal type automated apparatus to realize the operation that a small amount of chemical is distributed widely by inclining the culture container, and similar effects are realized by diluting the chemical (or not diluting) and supplying a slightly larger amount (for example, until the entire cells are immersed in the chemical in horizontal state). However, when a large amount of chemical is used, cells may be destroyed, and such method is not recommended.

On the other hand, in the field of regenerative medicine, to be liberated from shortage of donors or immunological rejection due to use of autologous cells, cell cultivation in various clinical departments or cell cultivation of a large amount may be needed in future.

It is hence an object of the invention to provide an automatic cell cultivation apparatus capable of conveying culture containers, exchanging culture medium, and operating other tasks promptly by using a multijoint robot.

SUMMARY OF THE INVENTION

To solve the problems, the automatic cell cultivation apparatus having a multijoint robot of the present invention comprises a cultivation apparatus main body for cultivating cells in one or more culture containers, the cultivation apparatus main body being equipped with one or more incubators accommodating the one or more culture containers, a chemical suction machine for sucking chemicals in the culture container, and a multijoint robot for conveying the culture container, wherein the multijoint robot has functions of conveying the culture container, detaching and attaching the lid of the culture container, and inclining the container when sucking chemicals in the culture container. As just described, by using the multijoint robot, the culture container is conveyed, the culture container lid is removed or put on, and the container is inclined when sucking the chemical in the culture container, and thus the cell cultivation operation can be carried out promptly by using only one robot.

In this automatic cell cultivation apparatus, a chemical feeder for feeding chemicals into the culture container may be further provided in the cultivation apparatus main body, and the multijoint robot may have a function of inclining the culture container two-dimensionally when feeding a small amount of chemicals into the cell container by the chemical feeder. Thus, a small amount of chemicals can be distributed in the entire culture container by inclining the container two-dimensionally when supplying chemicals into the culture container.

Further, in the automatic cell cultivation apparatus, the multijoint robot may be provided with a gripping hand having gripping hand members which open and close oppositely, leading end portions of the respective gripping hand members are formed in a rectangular shape in section, and a plurality of corners for gripping the circular portion of the culture container may be formed in the respective rectangular shapes. Thus, cylindrical culture containers of different diameters can be handled stably.

In the automatic cell cultivation apparatus, driving means for opening and closing the gripping hand members may be a pneumatic driving means. Thus, gripping force of the culture container can be stabilized easily.

The automatic cell cultivation apparatus further may comprise a cell image acquiring device for acquiring a cell image in the culture container from the bottom side of the culture container, wherein the cell image acquiring device may have an image recognition function for image recognizing exfoliation of the cell from the bottom of the culture container based on the acquired image, and also may have a function of checking the image recognition at plural positions of the culture container. Thus, exfoliation of cells from the culture container is recognized automatically, and subculture and other cell cultivation operation can be progressed.

In the automatic cell cultivation apparatus, a cultivation operation unit for allocating the chemical suction machine and the chemical feeder may be provided in the cultivation apparatus main body. The cultivation operation unit may be opened or closed by one or more sealing doors, and also a sterilization device may be provided for autoclave sterilization of inside of the cultivation operation unit. Thus, contamination can be prevented by autoclave sterilization.

In the automatic cell cultivation apparatus, the multijoint robot is provided with a gripping hand having gripping hand members which open and close oppositely, and leading end portions of the respective gripping hand members may be formed in a rectangular shape in section. Tapers each having circular section gradually increasing in diameter may be formed at the base side of the respective rectangular shapes, and insertion holes for inserting the gripping hand members may be formed in the door of the cultivation operation unit. Moreover, seal mechanisms for sealing the surrounding of the respective gripping hand members may be provided between the insertion holes and gripping hand members when the respective gripping hand members are inserted into the respective insertion holes. Thus, the leading end portions of the gripping hand members can be sterilized by autoclave in the inside of the cultivation operation unit.

Having the means as mentioned above, the automatic cell cultivation apparatus according to the invention uses the multijoint robot of high degree of freedom not only in conveying operation of culture containers but also in cultivation operation, and dedicated machines are not needed, and the cost is lowered, work operations of skilled workers difficult for dedicated machines can be reproduced, and contamination can be highly prevented.

BRIEF DESCRIPTION OF THE DRAWINGS

FIGS. 7 (a) and (b) are perspective views showing an example of operation of a multijoint robot of the automatic cell cultivation apparatus of the invention.

EMBODIMENTS

Figure 1:
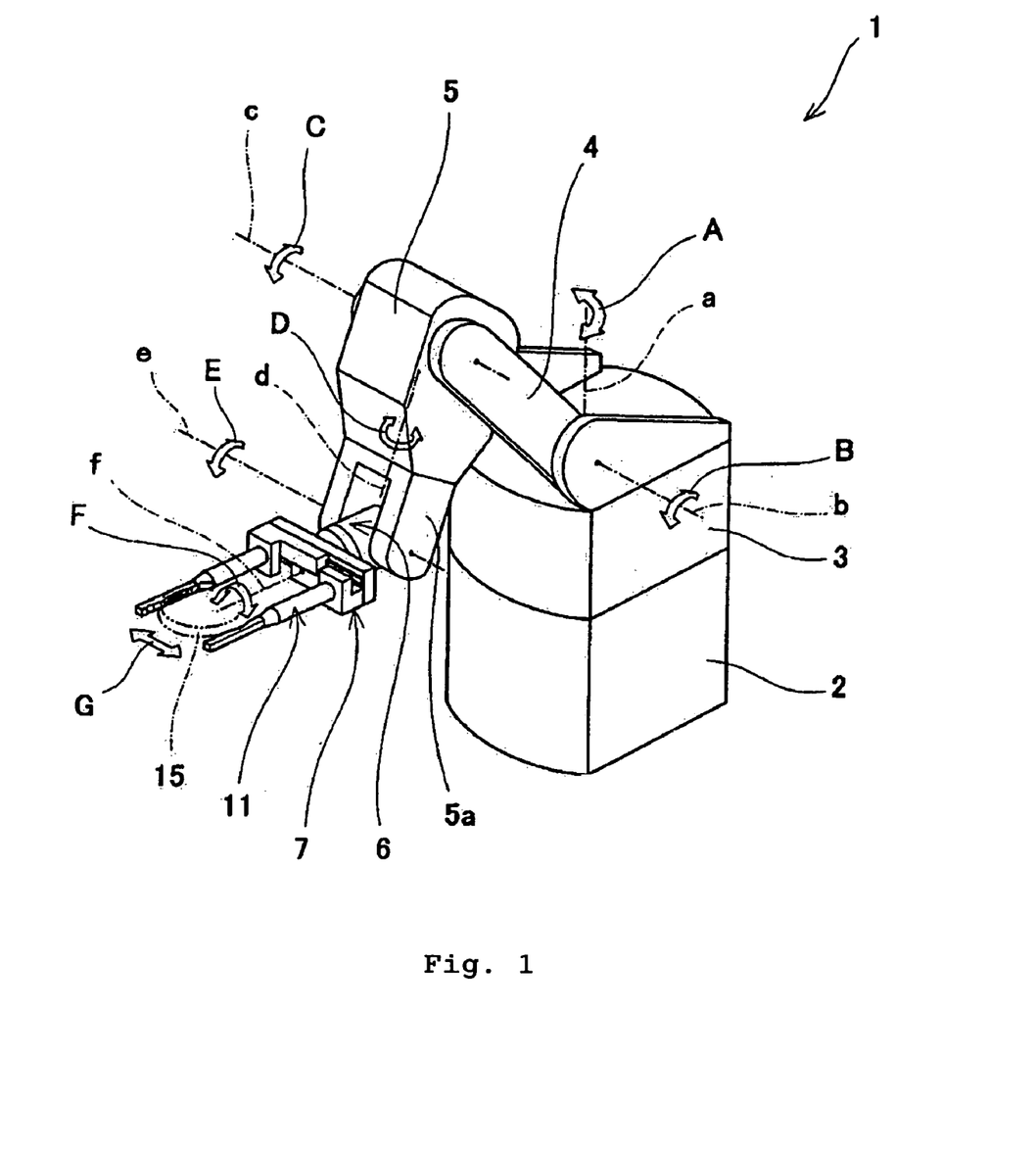
FIG. 1 is a perspective view showing an embodiment of a multijoint robot provided in an automatic cultivation apparatus of the invention.
Figure 2:
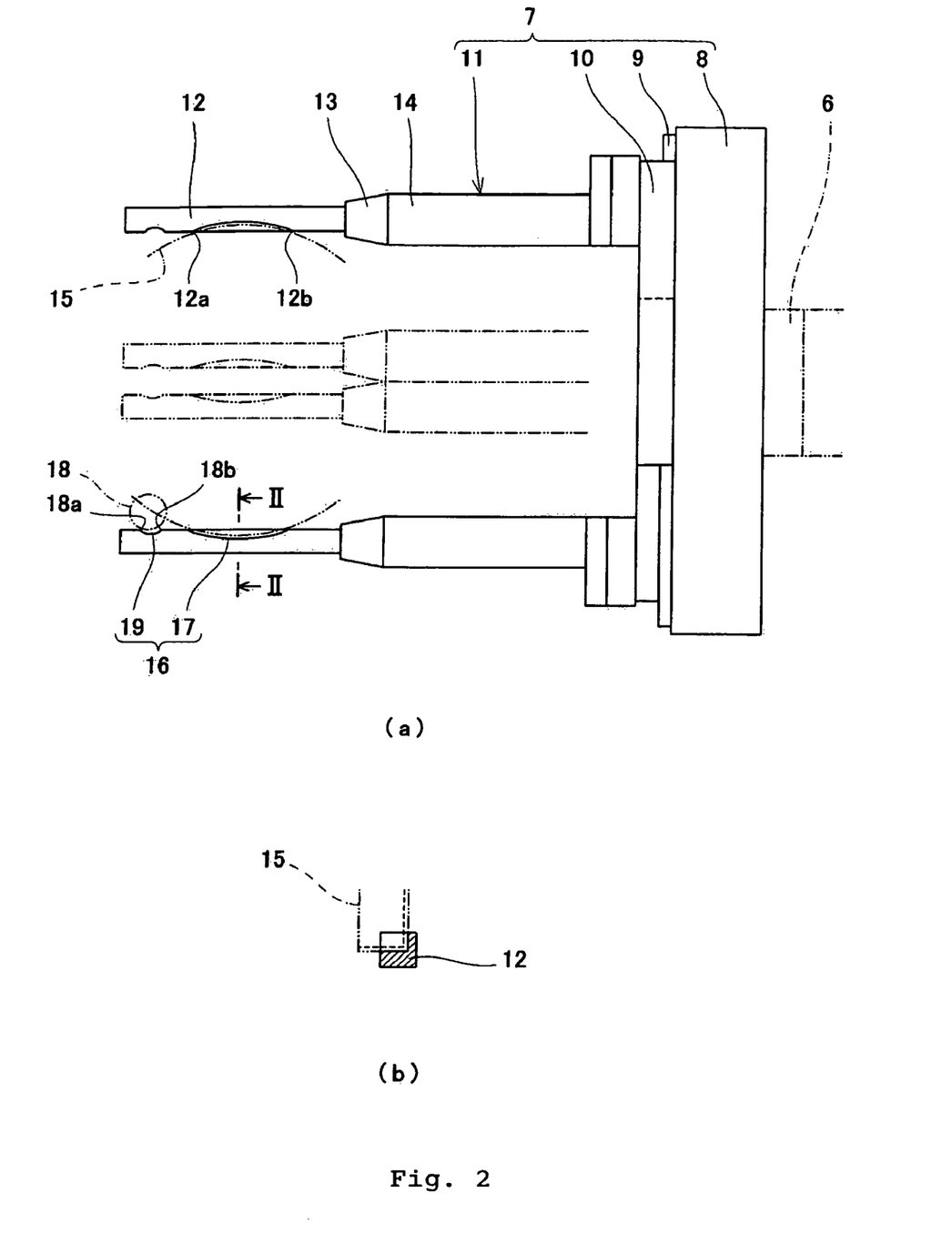
FIG. 2 is a drawing showing a gripping hand of the multijoint robot shown in FIG. 1, (a) being a plan view, and (b) being a cross-sectional view taken in the direction of arrows substantially along the line II-II.
Figure 3:
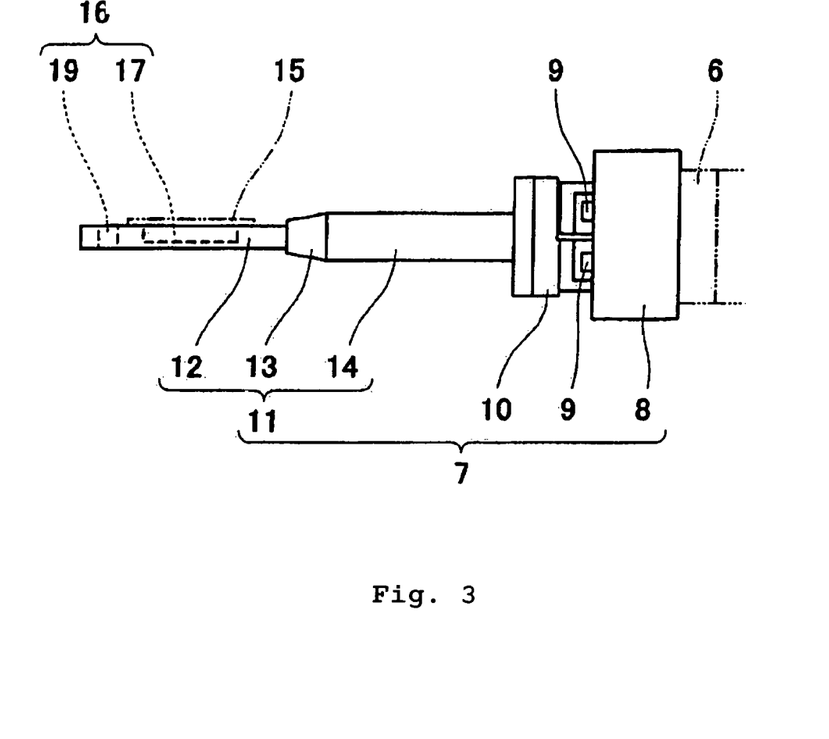
FIG. 3 is a side view of the gripping hand shown in FIG. 2.
Figure 4:
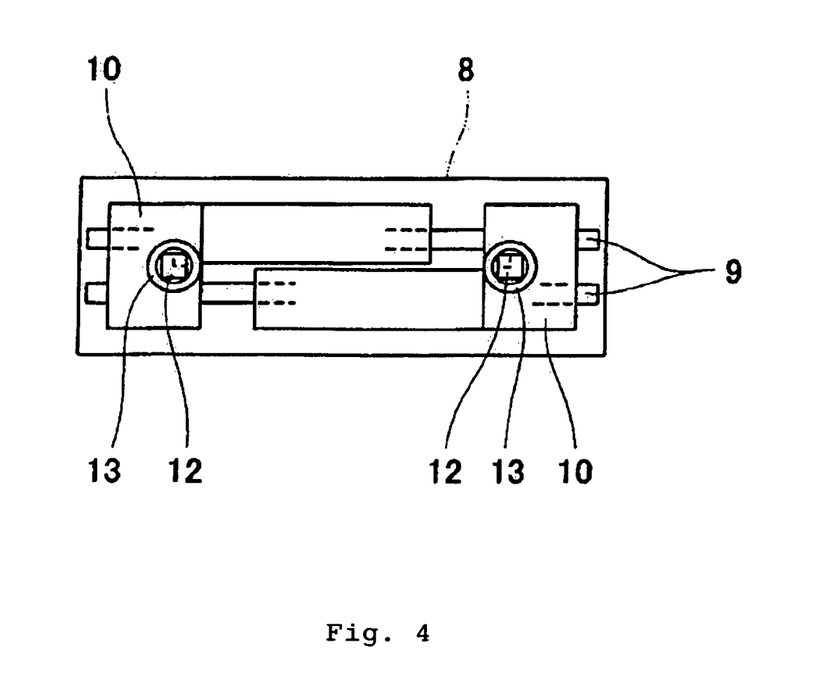
FIG. 4 is a front view of the gripping hand.

Embodiments are explained below while referring to the accompanying drawings. FIG. 1 is a perspective view showing an embodiment of a multijoint robot used in the automatic cultivation apparatus of the invention, and FIG. 2 is a drawing showing a gripping hand of the multijoint robot shown in FIG. 1, (a) being a plan view, and (b) being a cross-sectional view taken in the direction of arrows substantially along the line II-II. FIG. 3 is a side view of the gripping hand shown in FIG. 2, and FIG. 4 is a front view of the gripping hand. The multijoint robot is described below according to these drawings.

As shown in FIG. 1, the multijoint robot 1 comprises a base 3 which swivels on a fixing part 2 in the horizontal plane around axis (a), a first arm 4 which is inclinable above the base 3 in the vertical plane around axis (b), a second arm 5 which is inclinable at the leading end side of the first arm 4 in the vertical plane around axis (c), a second arm leading end 5a (U-shaped leading end in the drawing) which is rotatable at the leading end of the second arm 5 around axis (d), and a hand 6 which is inclinable at the leading end side of the second arm leading end 5a in the vertical plane around axis (e). The hand 6 also is configured to be rotatable around axis (f), and a gripping hand 7 is attached to its leading end. The gripping hand 7 is comprised of opposite arm members 11 that move close to or away from each other.

By using this multijoint robot 1, as indicated by arrows A to F corresponding to the above-described axes and arrow G in FIG. 1, various operations can be carried out by one robot, such as swiveling of the base 3 (arrow A), inclining of the first arm 4 (arrow B), inclining of the second arm 5 (arrow C), rotating of the arm leading end 5a (arrow D), inclining (arrow E) and rotating (arrow F) of the hand 6, width adjusting of the gripping hand (arrow G), in a total of 7 degrees of freedom (or 6 degrees of freedom for positioning). As far as multijoint robot 1 has such degrees of freedom, other structure can be adopted.

As shown in FIG. 2 to FIG. 4, the gripping hand 7 includes a support member 8 fixed in the hand 6, a linear guide 9 provided at the front side of the support member 8, a slide member 10 which may slide along this linear guide 9, and an arm member 11 fixed in the slide member 10. Accordingly, the support member 8 is rotatably adapted by rotation of front end portion of the hand 6, and the slide members 10 on which the arm members 11 are mounted slide along the linear guide 9 provided at the front side of the support member 8 so as to move close to or away from each other (in vertical direction as indicated by double dot chain line in FIG. 2).

A rectangular part 12 having prescribed length and rectangular section is formed at the leading end of the arm member 11, and a taper 13 with circular section gradually increasing in diameter is formed at the base of this rectangular part 12. A circular part 14 of prescribed length having circular section of prescribed diameter is formed at the base side of this taper 13. This circular part 14 is fixed so as to be orthogonal to the sliding direction of the slide member 10.

The rectangular part 12 has a gripping part 16 for gripping and holding a culture container 15 (dish). The gripping part 16 is composed of a container gripping part 17 for gripping the culture container 15, and a tube gripping part 19 for gripping a centrifugal tube 18, pipets or the like.

The container gripping part 17 is, as shown in FIGS. 2 (*a*) and (*b*), formed by partially cutting off in an arc shape in the inside upper part of the opposing rectangular parts 12. This cut-off arc is formed as an arc shape capable of supporting by contacting with the culture container 15 at two points of respective corners 12*a*, 12*b* of both ends when gripping the culture container 15. That is, the arc is formed in a smaller diameter than the outside diameter of the culture container 15.

Further, by cutting off only the inside upper part as shown, the container gripping part 17 is designed to support the downside of the culture container 15, or upside of the 15*a* (FIG. 7) by the portion remaining in the lower part of this cut-off part. In FIG. 2, the inside upper part of the rectangular part 12 is cut off, but since this gripping hand 7 is rotatable, when rotated by 180 degrees, the inside lower part is cut off.

The tube gripping part 19 is formed consecutively in the vertical direction inside of the opposite rectangular parts 12 as shown in the drawing, and is formed in an arc so as to support by contacting at two points at corners 18*a*, 18*b* of both ends when gripping the centrifugal tube, pipet or the like. That is, the arc is formed in a smaller diameter than the outside diameter of the centrifugal tube 18, pipet or the like.

Figure 5:
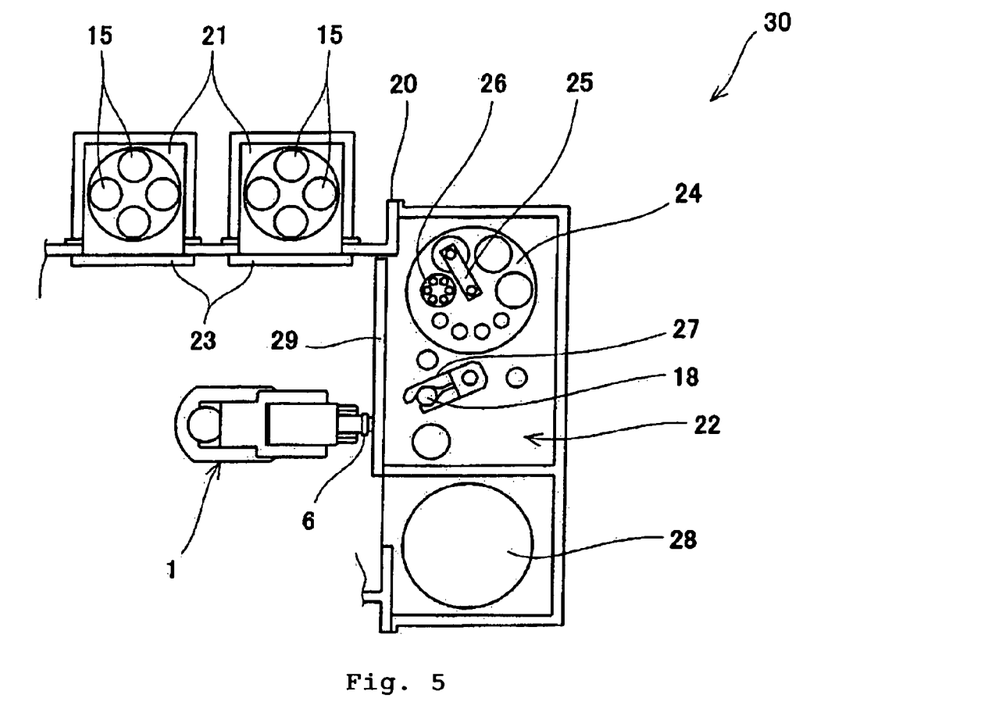
FIG. 5 is a plan view showing a part of an automatic cell cultivation apparatus having the multijoint robot shown in FIG. 1.
Figure 6:
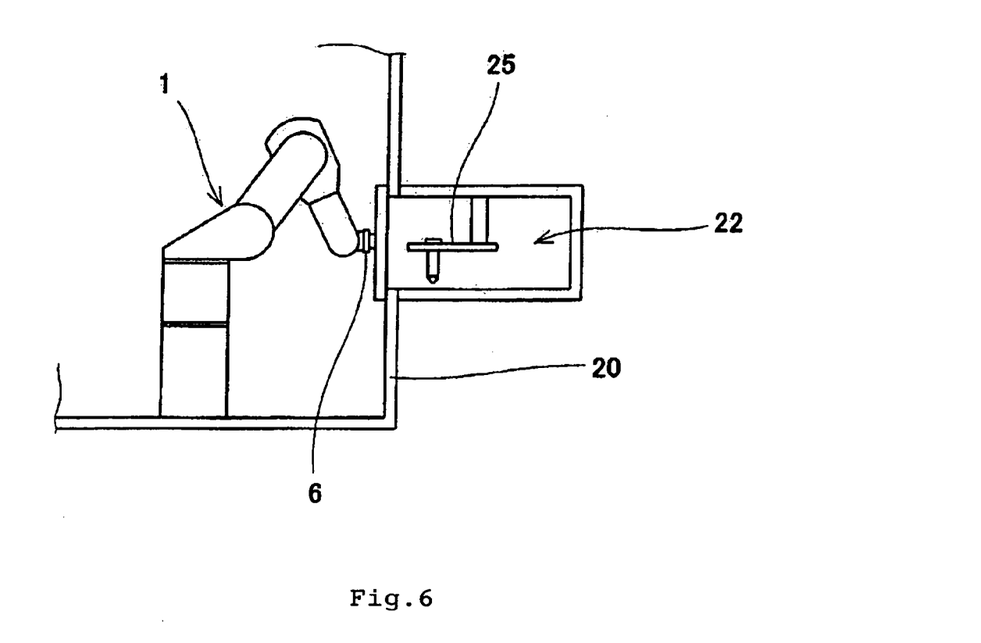
FIG. 6 is a longitudinal sectional view of the automatic cell cultivation apparatus shown in FIG. 5.

FIG. 5 is a plan view showing a part of an automatic cell cultivation apparatus having the multijoint robot shown in FIG. 1, and FIG. 6 is a longitudinal sectional view of the automatic cell cultivation apparatus. An example of automatic cell cultivation apparatus having a multijoint robot is explained below by referring to these drawings.

As shown in the drawings, the cultivation apparatus main body 20 having the multijoint robot 1 includes an incubators 21, and a cultivation operation unit 22. The incubators 21 are provided with doors 23 so as to seal up in a state of containing a plurality of culture containers 15. The cultivation operation unit 22 includes a turntable 24, a pipetting device 25, a pipet tip stand 26, and a centrifugal tube handling device 27. The pipetting device 25 works as suction apparatus of chemicals and feeder of chemicals, and has functions of culture medium discharge apparatus for discharging culture medium (chemicals) in culture container 15, culture medium feeder for supplying culture medium (chemicals) into culture container 15, and chemicals feeder for supplying cell exfoliating agent (chemicals) into culture container 15.

At the side (lower side in the drawing) of this cultivation operation unit 22, a centrifuge 28 is provided for separating cells and chemicals or other liquid, from the materials transferred into the centrifugal tube 18 by the centrifugal tube handling device 27.

In this embodiment, the door 29 is provided for sealing the cultivation operation unit 22, and when this door 29 is closed, the cultivation operation unit 22 is close tightly. By closing the door 29, only the inside of the cultivation operation unit 22 can be sterilized by autoclave. This autoclave sterilization is executed by high-pressure steam supplied from sterilization apparatus not shown in the drawing.

In the automatic cell cultivation apparatus 30 having a multijoint robot of such configuration, main operations are described below.

Figure 7:
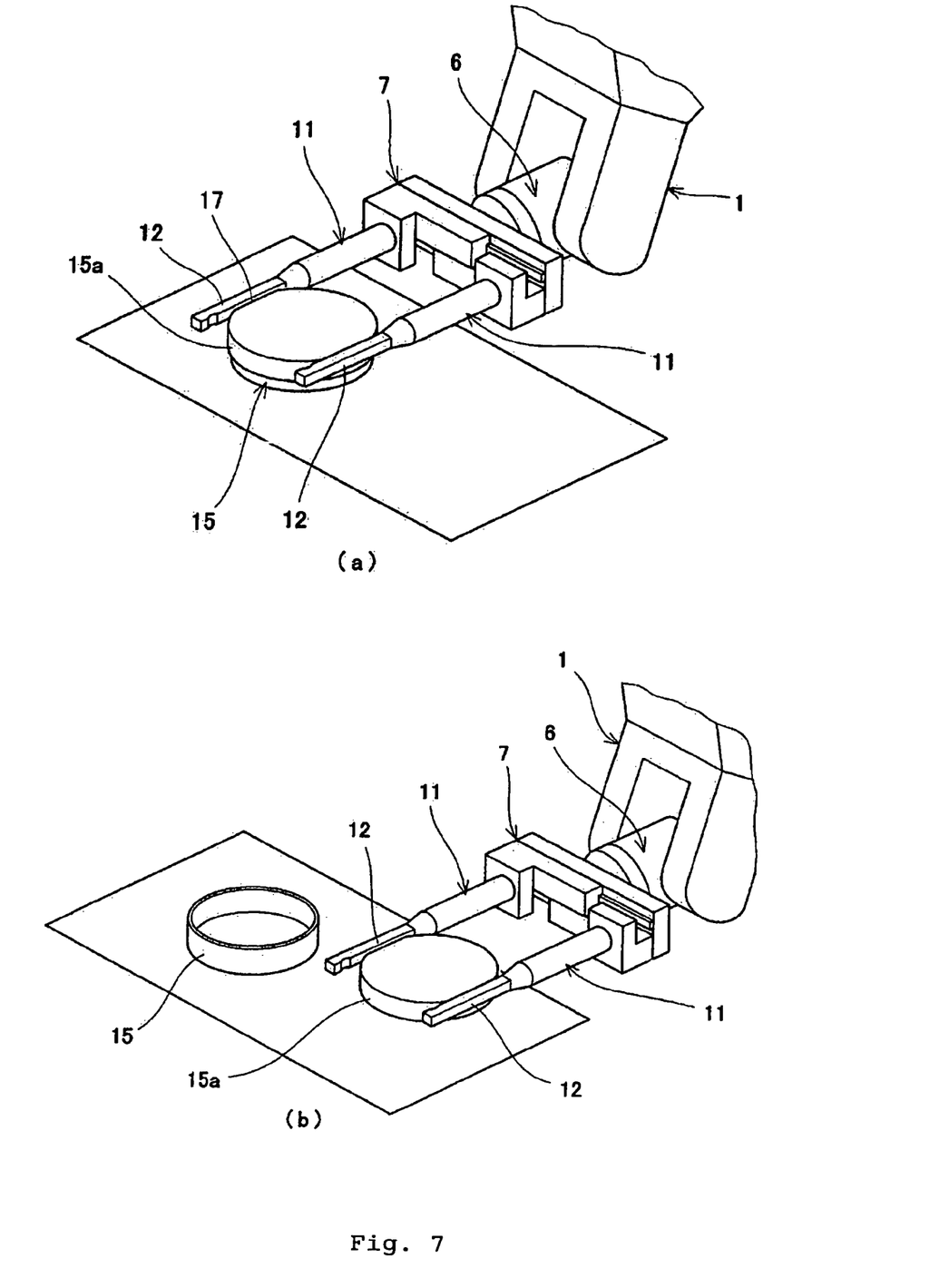

FIGS. 7 (*a*) and (*b*) are perspective views showing an example of operations of a multijoint robot of the automatic cell cultivation apparatus of the invention. Theses operations include attaching and detaching of lid of culture container. As shown in FIG. 7 (*a*), the culture container 15 is put in the place of operation, and the lid 15*a* is gripped by turning down the container gripping part 17 of the arm member 11 provided in the gripping hand 7 of the multijoint robot 1, and the lid 15*a* of the culture container 15 is opened or closed by controlling the motion of the hand 6.

By using the multijoint robot 1, after putting the culture container 15 carried by the gripping hand 7 of the robot 1 into the cultivation operation unit 22, the lid 15*a* is removed by using the same gripping hand 7, thereby the lid can be removed without using any dedicated machine.

Figure 8:
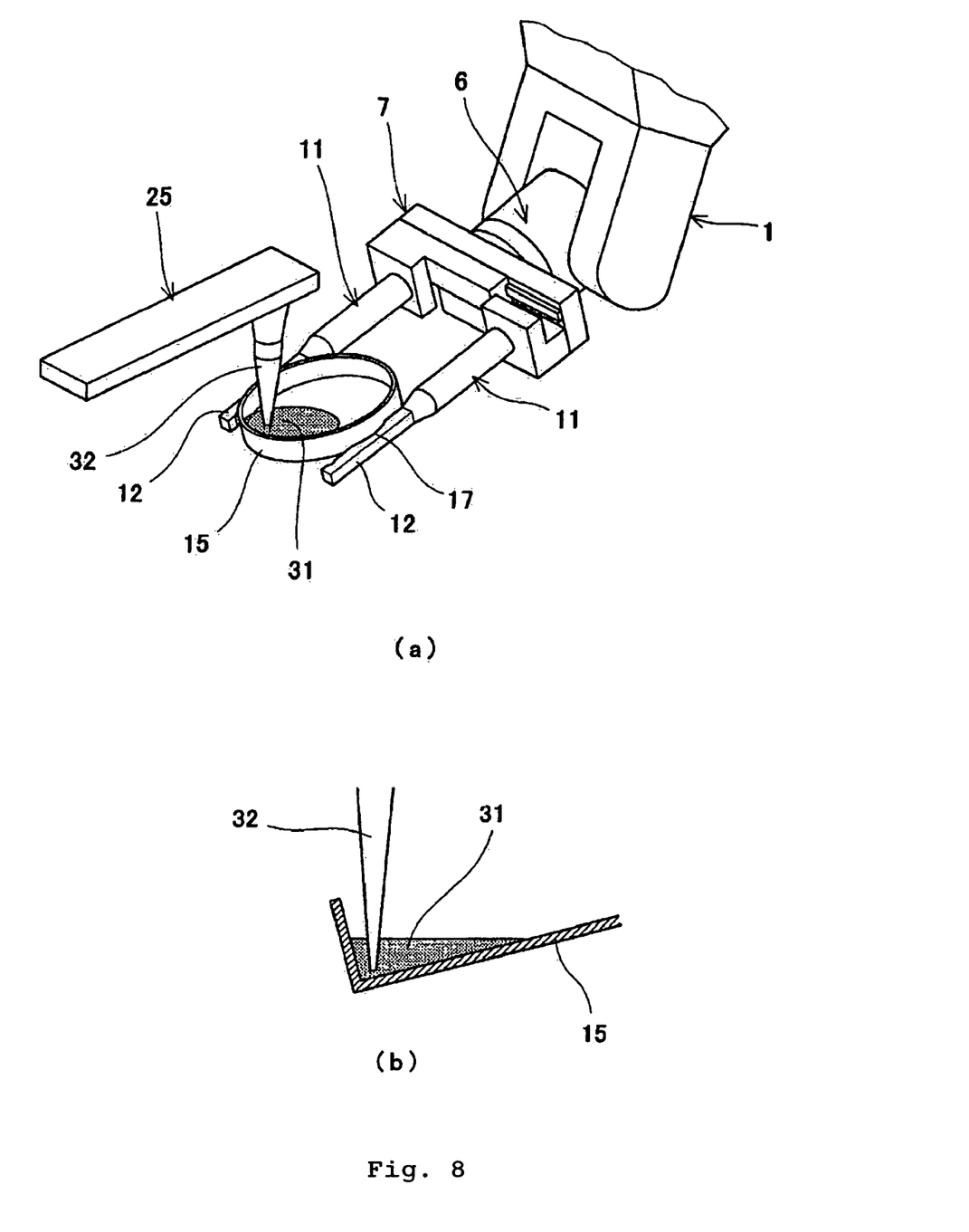
FIG. 8 is a drawing showing another example of operation of the multijoint robot of the automatic cell cultivation apparatus of the invention, (a) being a perspective view and (b) being a schematic view of longitudinal section of side view.

FIG. 8 is a drawing showing another example of operation of a multijoint robot of an automatic cell cultivation apparatus of the invention, (a) being a perspective view and (b) being a schematic view of longitudinal section of side view. This operation is inclination of container when exchanging the culture medium. When sucking and discharging the used culture medium 31 from the culture container 15, because the used culture medium 31 must be sucked out as much as possible and then discharged, the culture container 15 is inclined, as shown in FIG. 8 (*b*), and the used culture medium 31 is sucked out from the corner of the container 15.

In this case, as shown in FIG. 8 (*a*), the culture container 15 is gripped by the container gripping part 17 of the arm member 11 attached to the gripping hand 7 of the multijoint robot 1, the culture container 15 is inclined at prescribed angle by controlling the motion of the hand 6, and the pipet tip 32 provided at the leading end of the pipet (suction means) of culture medium discharge machine (25) is positioned at the lower corner of the culture container 15 as shown in FIG. 8 (*b*), and the used culture medium 31, chemicals, etc. can be sucked out as much as possible and then discharged.

Figure 9:
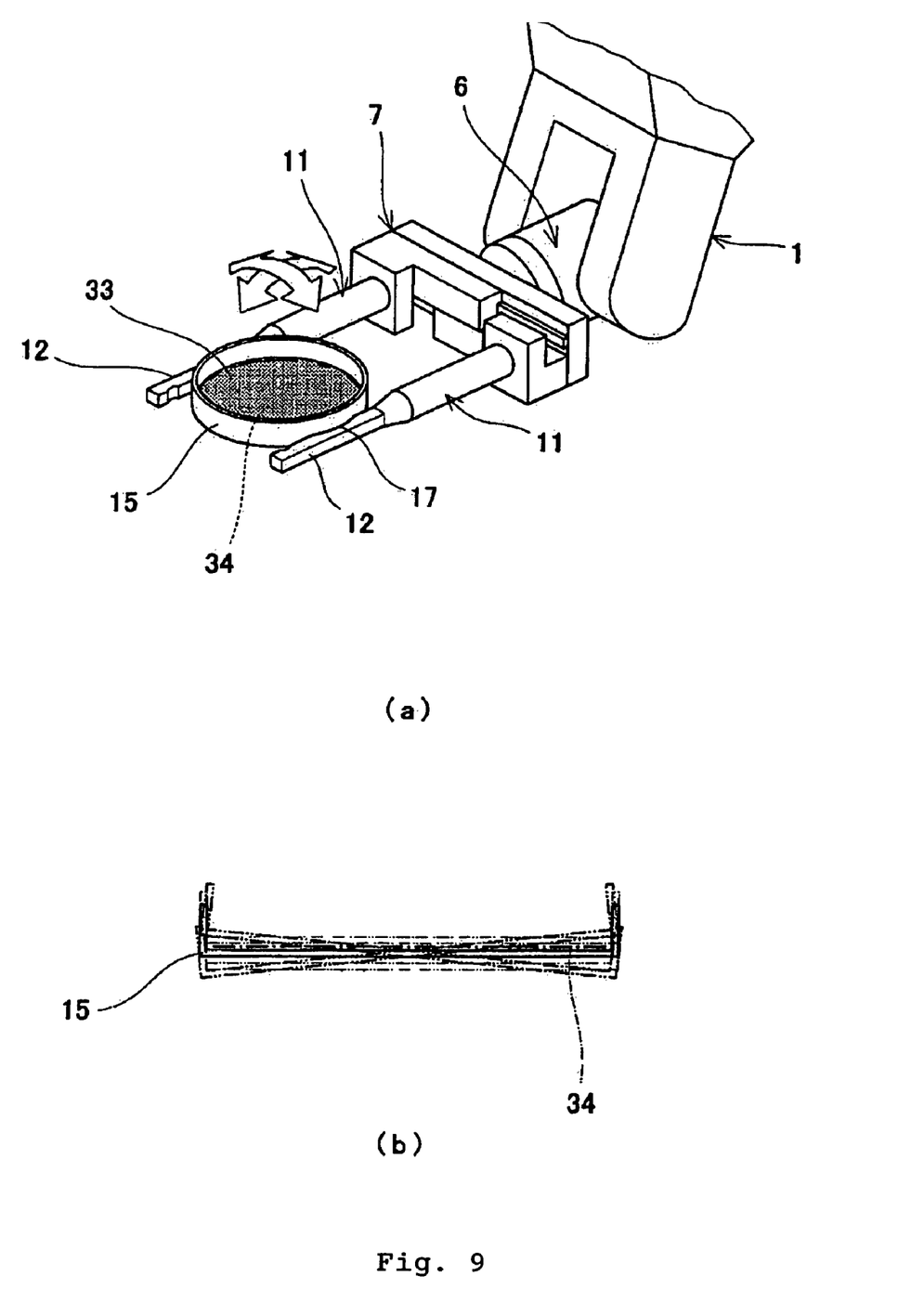
FIG. 9 is a drawing showing another example of operation of the multijoint robot of the automatic cell cultivation apparatus of the invention, (a) being a perspective view and (b) being a partial sectional view of side view.

FIG. 9 is a drawing showing another example of operation of the multijoint robot of the automatic cell cultivation apparatus of the invention, (a) being a perspective view and (b) being a partial sectional view of side view. This operation is two-dimensional inclination of container when supplying chemicals for exfoliating.

In subculture operation of cells cultivated in culture container 15 (dividing cells grown in the culture container 15 into plural culture containers), a small amount of exfoliation chemicals 33 (usually trypsin is used which is a digestive enzyme) is used, thereby the cells sticking to the bottom of the culture container 15 are exfoliated. Since the exfoliation chemicals 33 are harmful for cells in cultivation, a small amount must be used as far as possible, and processing should be done in a short time as soon as possible. To distribute the small amount of the exfoliation chemical throughout the culture container 15 in a short time, it is essential operation to incline the culture container 15 two-dimensionally.

In this embodiment, by inclining the culture medium 15 two-dimensionally (by inclining the surrounding of culture container 15 as shown in FIG. 9(*b*)) using the hand 6 of the multijoint robot 1, it is possible to incline in a similar manner as operation of a skilled worker, thereby consumption of the chemicals can be minimized.

Thus, by the automatic cell cultivation apparatus 30 having the multijoint robot 1, the multijoint robot 1 can be used not only in conveying of culture medium 15, but also in detaching and attaching of lid 15a of culture container 15, inclination of culture medium 15 when sucking the culture medium, two-dimensional inclination of culture medium 15 when supplying exfoliation chemicals, and in other various operations of cell cultivation, thereby extra special machines are not needed. In addition, the automatic cell cultivation apparatus 30 is simplified and the automatic cell cultivation apparatus 30 is provided at low cost. Moreover, since the apparatus is simple, sources of contamination are decreased, and therefore it is resistant to contamination. Further, jobs by skilled worker difficult for special machines can be also reproduced, and complicated connection of plural machines is not needed for an operation, and the motion control can be simplified.

Additionally, in subculture of cells, because only a small amount of chemical is used, destruction of cells or lowering of cell activity by excessive use of chemicals can be prevented.

In this subculture operation, cells exfoliated from the culture container 15 are transferred into the centrifugal tube 18, and this centrifugal tube 18 is conveyed to the prescribed position of the centrifuge 18. The centrifugal tube 18 is conveyed in a state of stably gripped by the gripping part 19 formed in the gripping hand 7 of the multijoint robot 1.

Cells in the centrifugal tube 18 thus conveyed into the centrifuge 28 are isolated from the liquid such as chemicals by centrifugal separation. The separated supernatant liquid is discarded, and cells remaining in the lower part are transferred into a culture container 15 provided with a fresh culture medium. This operation is done inside of the cultivation operation unit 22.

As means for recognizing automatically that cells are exfoliated from the culture container 15 by supplying chemicals, it may be considered to recognize by the lapsed time since supply of chemicals, but the optimum lapse of time varies depending upon every occasion such as the age of donor of cells, cultivation environment, and so on. It is hence impossible to recognize the optimum exfoliated state by mere lapse of time only.

Figure 10A:
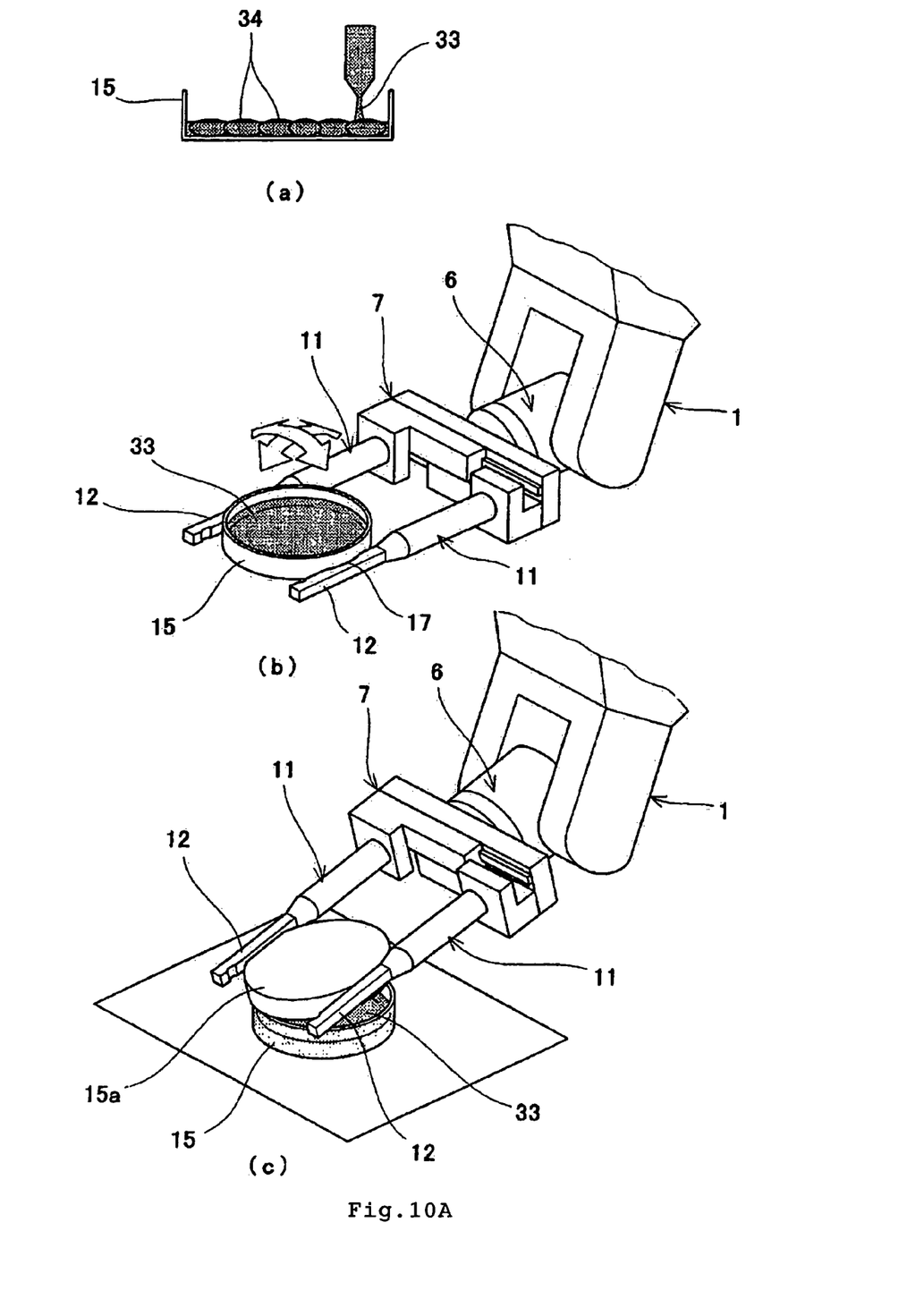
FIGS. 10A (a) to (c) are schematic diagrams of first half of example of cell exfoliation checking method in the automatic cell cultivation apparatus of the invention.

Method of recognizing that cells are exfoliated from the culture container 15 will be explained. FIGS. 10A (a) to (c) are schematic diagrams of first half of example of cell exfoliation showing the method in automatic cell cultivation apparatus of the invention, and FIGS. 10B (a) to (c) are schematic diagrams of second half of example of cell exfoliation showing the method in automatic cell cultivation apparatus of the invention.

First, when exfoliating the cells from the culture container 15 as mentioned above, exfoliation chemicals 33 (for example, trypsin) are supplied into the culture container 15 [FIG. 10A (a)]. Then, the culture container 15 is gripped by the gripping hand 6 provided on the hand 6 of the multijoint robot 1, and inclined two-dimensionally so that the supplied exfoliation chemicals 33 may be distributed throughout the culture container 15 [FIG. 10A (b)]. Thus, because it is preferred to process in a short time by using a small amount as far as possible owing to the harmfulness of the exfoliation chemicals 33 for cells in cultivation, the operation of skilled worker for distributing the exfoliation chemicals throughout the culture container 15 is realized by the multijoint robot 1.

As the exfoliation of the cultured cells from the bottom of the culture container 15 are gradually occurred by the effect of the exfoliation chemicals 33, the time from supply (addition) of the exfoliation chemicals 33 until the exfoliation can be preliminarily measured by experiment, and two-dimensional inclination of the container is carried out by the multijoint robot 1 in a shorter time than that time so that the exfoliation chemicals 33 may be distributed throughout the culture container.

Then, the culture container 15 is placed at prescribed position, and the lid 15a of culture container 15 is gripped by the gripping hand 7 of the robot, and put on the top of the culture container 15 to close [FIG. 10A (c)]. Or, the top of the culture container 15 may be closed by the lid 15a before the two-dimensional inclination operation [FIG. 10A (b)].

Figure 10B:
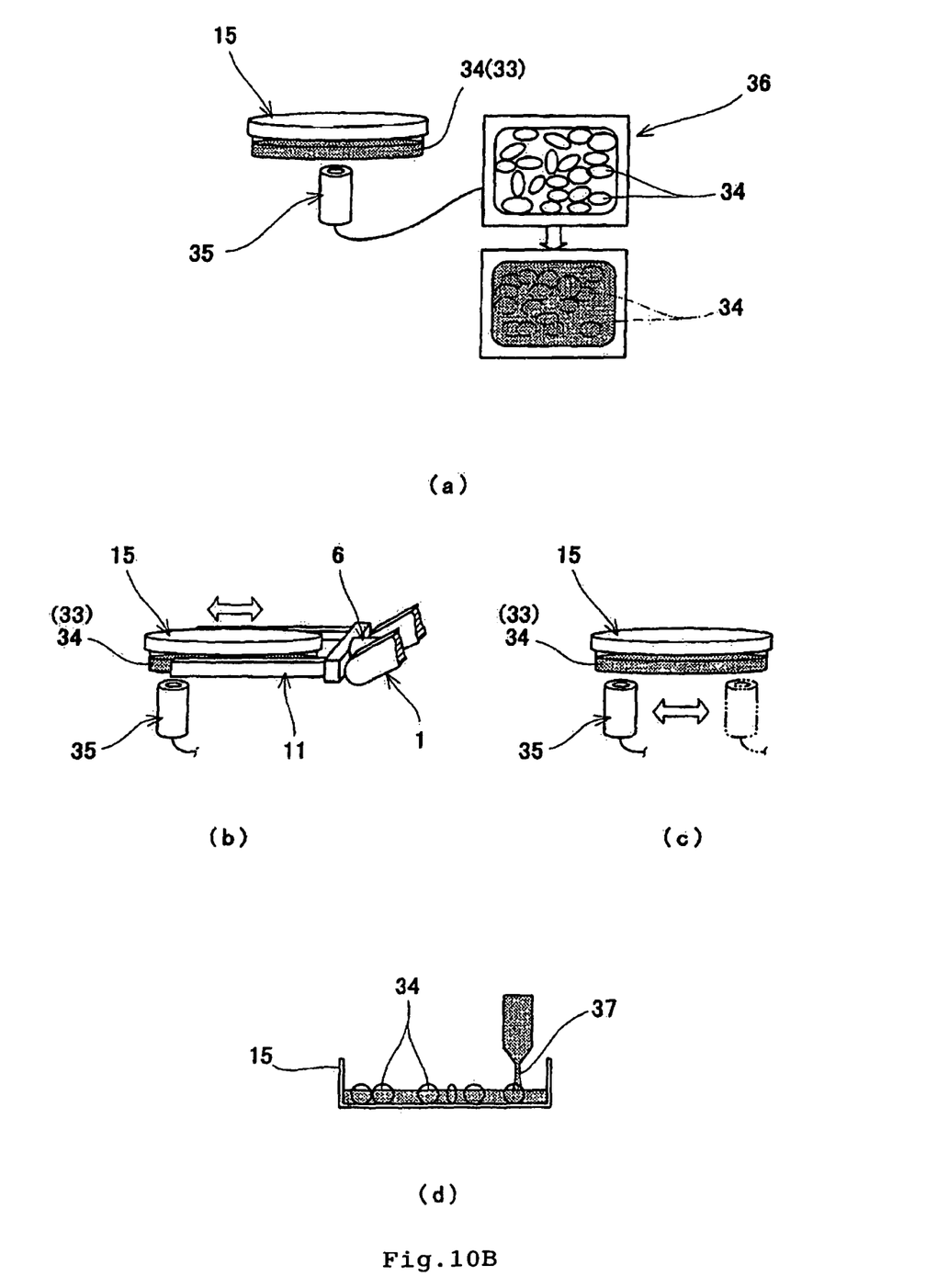
FIGS. 10B (a) to (c) are schematic diagrams of second half of example of cell exfoliation checking method in the automatic cell cultivation apparatus of the invention.

In this state, from the lower part of the culture container 15 closed with the lid 15a, the state of cells 34 is observed by observation device 36 including a camera 35 and others [FIG. 10B (a)]. If the observation device 36 including the camera 35 and others is installed at a remote position, the culture container 15 can be promptly conveyed to this position by controlling the position of the hand 6 of the robot.

The observation device 36 also functions as a cell image pickup device that has a function of picking up a cell image in the culture container 15 from the bottom side of the culture container 15. This cell image pickup device has a function of counting the number of cells per unit area from the obtained image, a function of judging necessity of subculture on the basis of this result, and a function of recognizing exfoliation of cells from the culture container bottom at the time of subculture by image recognition. By combining these functions, automation is easily realized. The observation device 36 may also include a personal computer. The image shown in the upper side of FIG. 10B (a) shows the cells 34 sticking to the culture container 15, and the image shown in the lower side of the Figure shows the cells 34 exfoliated from the culture container 15.

To confirm cells 34 are exfoliated, the following method may be considered. Because the size of cells is generally about 10 to 30 microns, and microscope or micro lens is needed for observation. But optical device of such high magnification factor is shallow in depth of focus, and therefore when the cells 34 are exfoliated from the bottom of the culture container 15, the position is deviated, so that the focus is not adjusted. When the cells 34 become thus hardly observed, it may be judged that the cells 34 are exfoliated from the bottom of the culture container 15. Among other methods, it may be detected by change of cell shape from slender shape of cells 34 when inoculated to circular shape after exfoliation of cells 34 (image recognition of cell change from slender to circular), or exfoliation from the bottom of the culture container 15 may be judged by a method of observing an extreme increase of moving distance of cells 34 when the culture container 15 is moved (detection of increase of cell moving distance). The lower image in FIG. 10B (a) shows a state out of focus due to change of shape from slender cells to circular cells.

Thus, when exfoliation of the cells 34 is recognized at one position of culture container 15, the culture container 15 is moved by the multijoint robot 1, and it is confirmed whether the cells are also exfoliated at other position [FIG. 10B (b)]. To check whether the cells 34 are exfoliated or not, the camera 35 may be moved within the range of bottom of the culture container 15 to observe other position [FIG. 10B (c)]. In this way, if the cell image pickup device has a function of checking images of plural positions of culture container 15, the exfoliation can be recognized at higher precision.

When exfoliation of the cells 34 is recognized in the entire culture container 15, an exfoliation inhibitor 37 (usually culture medium containing serum or trypsin inhibitor) is added in order to stop the effect of exfoliation chemicals [FIG. 10B (d)].

According to this cell exfoliation checking method, it can be automatically judged whether the cells are exfoliated from the bottom of the culture container 15 or not. What is more, the time of the cells 34 being exposed to the exfoliation chemicals 33 is minimized, and the cells 34 can be exfoliated from the bottom of the culture container 15 without causing destruction of culture cells or lowering of cell activation.

In this kind of cell cultivation apparatus, when cultivating different cells (cells from different subject), it is necessary to prevent contamination by sterilizing. In particular, the inside of the cultivation operation unit 22 requires a complete sterilization, and as mentioned above, the cultivation operation unit 22 is provided with the door 29, and only the cultivation operation unit 22 can be subjected in autoclave sterilization by closing the door 29 of the cultivation operation unit 22. When sterilizing to prevent contamination, it is also important to sterilize the gripping hand 7 which directly handles the culture container 15 and the centrifugal tube 18. In this embodiment, therefore, the leading end of the gripping hand 7 for griping the container and others are also autoclavesterilized completely.

As described above, in the multijoint robot, the rectangular parts 12 at the leading end side of the gripping hand 7 provided on the hand 6 is formed in a rectangular shape in section, and the base side of the gripping hand 7 is formed in a circular shape in section having prescribed diameter. Moreover, a taper 13 with circular shape in section gradually increasing in diameter is formed between the portion having the rectangular shape in section and the portion having the circular shape in section.

Figure 11:
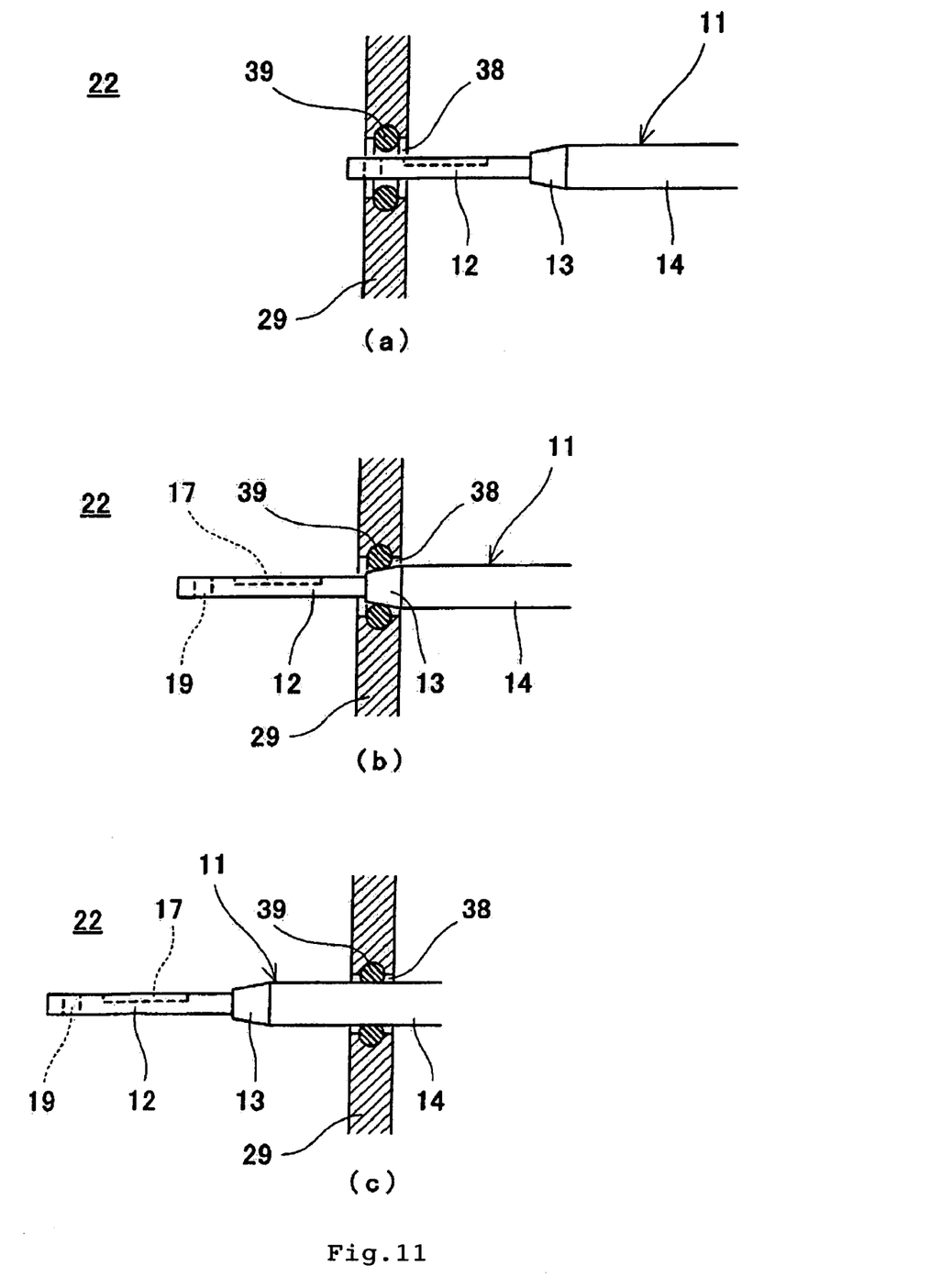
FIGS. 11 (a) to (c) are sectional views of sterilizing parts of gripping hand of the multijoint robot provided in the automatic cell cultivation apparatus of the invention.

On the other hand, as shown in FIG. 11 (*a*) to (*c*), showing sectional views of sterilizing parts of the gripping hand of multijoint robot provided in the automatic cell cultivation apparatus of the invention, the door 29 for closing the cultivation operation unit 22 has an insertion hole 38 of circular shape in section for inserting the leading end of arm member 11 of gripping hand 7. The insertion hole 38 is formed in a larger diameter than the outside diameter of circular part 14 of the arm member 11, and the inside of the insertion hole 38 includes a sealing member 39 such as O-ring in a slightly smaller diameter than the outside diameter of the circular part 14. This portion is the seal mechanism for sealing the surrounding of the gripping hand.

Thus, by forming the insertion hole 38 having the sealing member 39 in the door 29, as shown in FIG. 11 (*a*), when the leading end (rectangular part 12) of arm member 11 is inserted into the insertion hole 38 until the taper 13 abuts against the seal member 39 as shown in FIG. 11 (*b*), it is inserted in such a manner that the axle center of the arm member 11 is aligned so as to coincide with the axle center of the insertion hole 38. At this time, by adapting pneumatic driving as driving means for moving the arm member 11 close to or away from each other, dislocation can be absorbed when the taper 13 of the arm member 11 is inserted along the insertion hole 38 while being aligned with the axle center, thereby the insertion operation is carried out in a stable state.

As shown in FIG. 11 (*c*), when inserted further, the outer periphery of the circular part 14 is inserted in a state contacting with the seal member 39, and the arm member 11 is inserted in the closed state around the insertion hole 38. As a result, the leading end portion of the arm member 11 is positioned inside of the cultivation operation unit 22 closed by the door 29.

Figure 12:
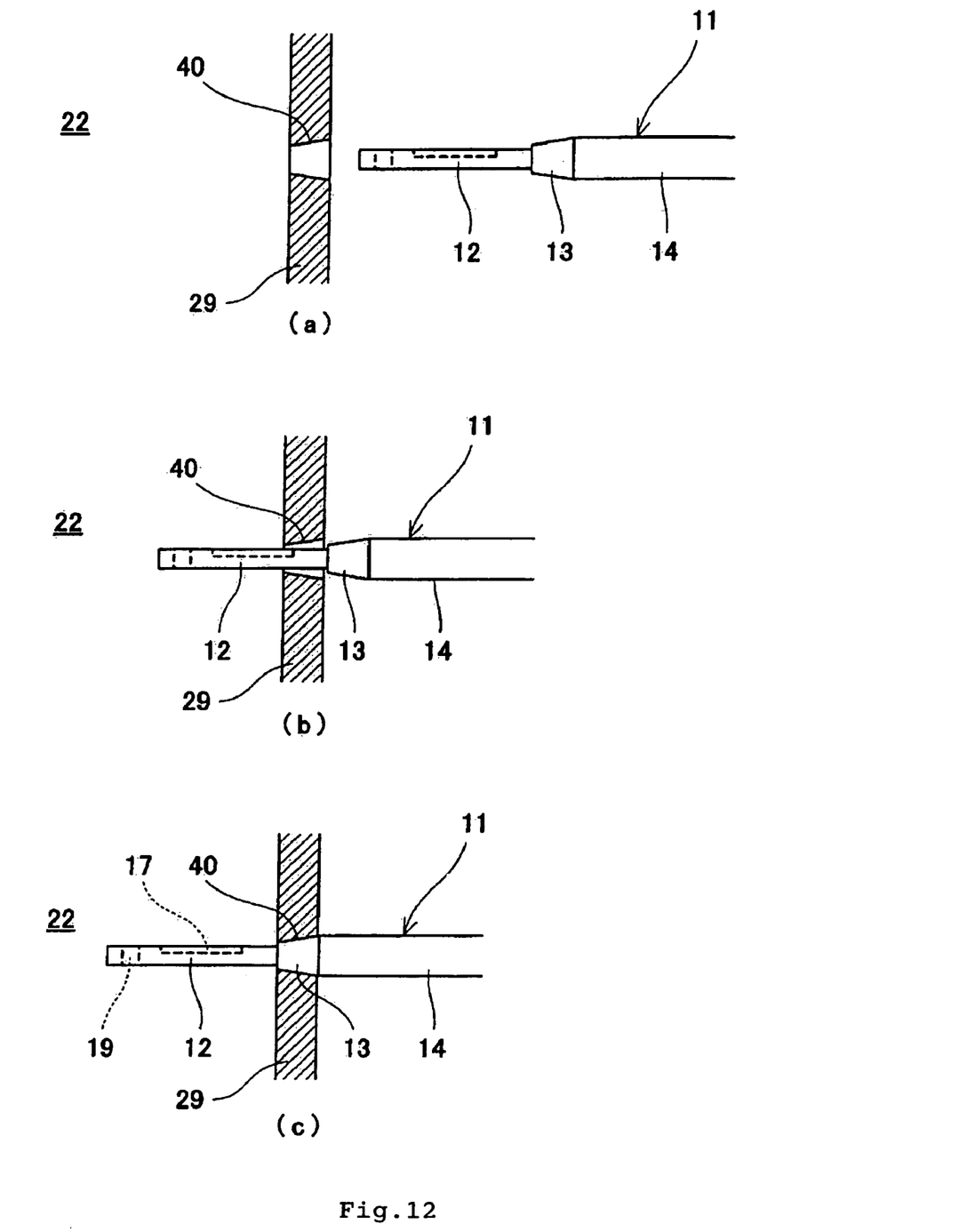
FIGS. 12 (a) to (c) are sectional views of further example of the sterilizing parts of the gripping hand of the multijoint robot provided in the automatic cell cultivation apparatus of the invention.

As shown in FIGS. 12 (*a*) to (*c*), showing sectional views of further example of the sterilizing parts of the gripping hand of the multijoint robot provided in the automatic cell cultivation apparatus of the invention, the door 29 for closing the cultivation operation unit 22 has a tapered insertion hole 40 matched with the shape of the taper 13 of the arm member 11 [FIG. 12 (*a*)], and when the leading end of the arm member 11 is inserted in this insertion hole 40 [FIG. 12 (*b*)], and further the taper 13 of the arm member 11 is inserted along the tapered insertion hole 40 while aligning in center, the arm member 11 can be inserted in such a state that the taper 13 is in contact with the tapered insertion hole 40 [FIG. 12 (*c*)]. This portion is the seal mechanism for sealing around the gripping hand. As a result, the leading end portion of the arm member 11 is positioned in the cultivation operation unit 22 closed by the door 29.

As shown in FIGS. 11 and 12, by subjecting the inside of cultivation operation unit 22 to autoclave sterilization in such a state that the leading end portion of arm members 11 positioned in the cultivation operation unit 22 closed by the door 29, together with all devices installed in the cultivation operation unit 22 such as turntable 24 and pipetting device 25, the container gripping parts 17 of the arm members 11 for gripping the culture container 15 and the tube gripping parts 19 for gripping the centrifugal tube 18 can be completely sterilized by autoclave. Therefore, contamination by arm members 11 contacting with the culture container 15 and others can be prevented in a stable state.

The components in the embodiment may be combined freely, and may be combined properly depending on the conditions of use or the like, and the invention is not limited to this embodiment alone.

The embodiment is intended only to show as examples, and the invention may be changed and modified within the scope not departing from the true spirit of the invention, and the invention is not limited to the illustrated embodiment alone.

The automatic cell cultivation apparatus of the invention is preferably used in the field for cultivating cells mechanically and efficiently, and cultivating a huge quantity of cells.

What is claimed is:

1. An automatic cell cultivation apparatus having a multijoint robot, comprising a cultivation apparatus main body for cultivating cells in one or more culture containers, the cultivation apparatus main body being equipped with one or more incubators accommodating the one or more culture containers, a chemical suction machine for sucking chemicals in the culture container, and a multijoint robot for conveying the culture container, wherein the multijoint robot has functions of conveying the culture container, detaching and attaching the lid of the culture container, and inclining the container when sucking chemicals in the culture container;

wherein the multijoint robot includes a gripping hand having gripping hand members operatively coupled to a linear slide and arranged to open and close in a linear direction, each of the gripping hand members including a leading end portion having a rectangular cross-section, each of the gripping hand members having a container gripping portion and a tube gripping portion;

the container gripping portion of each gripping hand member defined in part by a cut on an upper inside part of each leading end portion, the cut on each leading end portion forming a first pair of corners sized to engage a culture container at two points; and wherein the tube gripping portion of each leading end portion defined in part by a vertical arc formed on an inside part of each leading end portion, the vertical arc on each leading end portion forming a second pair of corners sized to engage a vertically oriented tube at two points.

2. The automatic cell cultivation apparatus having a multijoint robot according to claim 1, wherein a chemical feeder for feeding chemicals into the culture container is further provided in the cultivation apparatus main body, and the multijoint robot has a function of inclining the culture container two-dimensionally when feeding a small amount of chemicals into the cell container by the chemical feeder.

3. The automatic cell cultivation apparatus having a multijoint robot according to claim 1, wherein the gripping hand members are pneumatically actuated.

4. The automatic cell cultivation apparatus having a multijoint robot according to claim 2, further comprising a cell image acquiring device for acquiring a cell image in the culture container from the bottom side of the culture container, wherein the cell image acquiring device has an image recognition function for image recognizing exfoliation of the cell from the bottom of the culture container based on the acquired image, and also has a function of checking the image recognition at plural positions of the culture container.

5. The automatic cell cultivation apparatus having a multijoint robot according to claim 1, wherein a cultivation operation unit for allocating the chemical suction machine and the chemical feeder is provided in the cultivation apparatus main body, the cultivation operation unit is opened or closed by one or more sealing doors, and also a sterilization device is provided for autoclave sterilization of inside of the cultivation operation unit.

6. The automatic cell cultivation apparatus having a multijoint robot according to claim 5, wherein the gripping hand members each include tapers each having circular section gradually increasing in diameter and formed at the base side of the respective rectangular shapes, insertion holes for inserting the gripping hand members are formed in the door of the cultivation operation unit, and seal mechanisms for sealing the surrounding of the respective gripping hand members are provided between the insertion holes and gripping hand members when the respective gripping hand members are inserted into the respective insertion holes.

7. The automatic cell cultivation apparatus having a multijoint robot according to claim 2, wherein a cultivation operation unit for allocating the chemical suction machine and the chemical feeder is provided in the cultivation apparatus main body, the cultivation operation unit is opened or closed by one or more sealing doors, and also a sterilization device is provided for autoclave sterilization of inside of the cultivation operation unit.

8. An automatic cell cultivation apparatus, comprising:
a cultivation apparatus main body for cultivating cells in a culture container;
the cultivation apparatus main body being equipped with an incubator sized to accommodate the culture container;
a chemical suction machine arranged to extract material from the culture container;
a multijoint robot, the multijoint robot arranged to grasp the culture container, convey the culture container, detach and attach a lid of the culture container, and incline the culture container when the culture container is positioned to have material extracted by the chemical suction machine;
the multijoint robot further including:
a base arranged to swivel about a vertical axis;
a first arm mounted to the base and arranged to pivot about a first horizontal axis;
a second arm mounted to the first arm and arranged to pivot about a second horizontal axis;
the second arm including a leading end, the leading end arranged to swivel about a swivel axis, the swivel axis oriented orthogonal relative to the second horizontal axis;
a hand mounted to the leading end and arranged to pivot about a hand axis oriented orthogonal relative to the swivel axis; and
the hand including arm members, the arm members arranged to swivel relative to the hand about a hand swivel axis, the arm members further arranged to open and close in unison in opposite directions to grasp or release the culture container; and
each of the arm members including a cut forming a container gripping portion having two contact corners, the cut sized to have a radius less than a radius of a culture container, the two contact corners on each container gripping portion cooperating with the two contact corners of the container gripping portion on the other arm member to grip the culture container at a total of four contact points; and
each of the arm members further including a vertical arc-shaped cut forming a tube gripping portion having two contact corners, the vertical arc-shaped cut sized to have a radius less than a radius of a tube, the two contact corners on each tube gripping portion cooperating with the two contact corners of the tube gripping portion on the other arm member to grip the tube at a total of four contact points.

9. The apparatus of claim 8, wherein each of the gripper arms is formed from a rectangular cross-section, each of the cuts formed by removing a portion of an inside upper part of each arm member, the cut having a radius smaller than a radius of the culture container.

10. The apparatus of claim 8, wherein the arm members are mounted to a linear slide assembly.

11. An automatic cell cultivation apparatus, comprising:
a cultivation apparatus main body for cultivating cells in a culture container;
the cultivation apparatus main body being equipped with an incubator sized to accommodate the culture container;
a chemical suction machine arranged to extract material from the culture container;
a multijoint robot, the multijoint robot arranged to grasp the culture container, convey the culture container, and detach and attach a lid of the culture container;
the multijoint robot further comprising:
a base arranged to swivel about a vertical axis;
an arms assembly, the arm assembly mounted to the base and arranged to pivot about at least one horizontal axis;
a leading end mounted to the arm assembly and arranged to swivel about a leading end swivel axis, the leading end swivel axis oriented orthogonal relative to the at least one horizontal axis; and
a hand assembly mounted to the leading end and arranged to pivot about a hand assembly pivot axis oriented orthogonal relative to the leading end swivel axis, the hand assembly further including arm members arranged to swivel about an arm member swivel axis disposed orthogonal relative to the hand assembly pivot axis, the arm members coupled to a linear slide and arranged to open and close in unison to grasp or release the culture container;
wherein each of the arm members of the hand assembly includes a cut formed on an inside upper portion of each arm member and forming a first pair of corners, each of the arm members further including a vertical arc-shaped channel forming a second pair of corners, each cut sized to enable the first pair of corners to grip a container by the first pair of corners, each vertical cut sized to enable the second pair of corners to grip a tube by the second pair of corners;

wherein the multijoint robot is arranged to move the culture container about multiple degrees of freedom and further is arranged to tilt the culture container in two dimensions.

12. An automatic cell cultivation apparatus having a multijoint robot comprising a cultivation apparatus main body for cultivating cells in one or more culture containers, the cultivation apparatus main body further comprising:

one or more incubators accommodating the one or more culture containers;

a chemical suction machine for sucking chemicals in the culture container; and a multijoint robot for conveying the culture container;

wherein the multijoint robot is arranged to convey the culture container, detach and attach a lid of the culture container, and incline the culture container when sucking chemicals in the culture container;

wherein the multijoint robot is provided with a gripping hand having gripping hand members and rectangular parts each having a rectangular shape in cross-section formed at the leading end portions of the respective gripping hand members, and the respective rectangular parts have container gripping parts and tube gripping parts;

wherein each of the container gripping parts is formed by forming a cut on an inside upper part of the opposing rectangular parts, the cut sized to have a radius less than a radius of a culture container, the cut on each gripping hand member cooperating with the cut on the other gripping hand member to support a culture container by contacting the culture container at a total of four corners; and wherein each of the tube gripping parts is formed in an arc, the arc sized to have a radius less than a radius of a tubular instrument, the arc sized to have a radius less than a radius of a tubular instrument, the arc on each gripping hand member cooperating with the arc on the other gripping hand member to support a tubular instrument by contacting the tubular instrument at a total of four corners.

13. The apparatus of claim 12, wherein the cut formed on the inside upper part of the opposing rectangular parts comprises a partial arc-shaped cut.

* * * * *